United States Patent [19]

Biollaz

[11] 4,261,985
[45] Apr. 14, 1981

[54] NOVEL DIURETICS

[75] Inventor: Michel Biollaz, Riehen, Switzerland

[73] Assignee: Ciba-Geigy Corporation, Ardsley, N.Y.

[21] Appl. No.: 94,266

[22] Filed: Nov. 14, 1979

[30] Foreign Application Priority Data

Nov. 22, 1978 [CH] Switzerland ............ 11980/78

[51] Int. Cl.³ .................................. A61K 31/56
[52] U.S. Cl. ..................... 424/240; 260/397.47
[58] Field of Search ............ 424/240; 260/397.47

[56] References Cited

U.S. PATENT DOCUMENTS 3,250,792  5/1966  Wettstein et al. ............ 260/397.1

Primary Examiner—Elbert L. Roberts
Attorney, Agent, or Firm—Theodore O. Groeger

[57] ABSTRACT

An advantageous diuretic action by excretion of water, sodium and chloride ions, with reduced excretion of potassium ions, is effected by combined administration of a 19-oxygenated steroid compound of the pregnane series of the formula

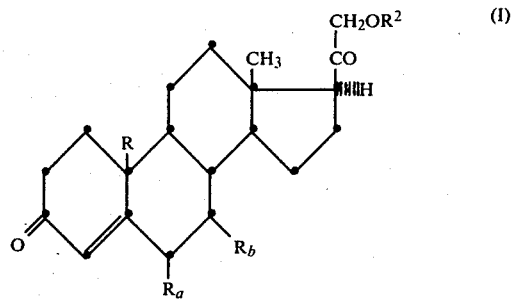

wherein
$R_a$ represents a hydrogen atom, and
$R_b$ represents an α-oriented lower alkanoylthio group, or
$R_a$ and $R_b$ together represent a carbon-carbon bond or an α- or β-oriented methylene radical,
R represents a free hydroxymethyl group or a hydroxymethyl group etherified by a lower alkyl or esterified by a lower alkanoyl; or represents a carboxyl group or a lower alkoxycarbonyl group, and
$R^2$ represents a hydrogen atom or the acyl radical Ac of a carboxylic acid, as the aldosterone-antagonising component A on the one hand, and, on the other hand, of a conventional diuretic which is unspecific in respect of electrolyte excretion, e.g. a diuretically effective derivative of benzothiadiazine, benzenesulfonamide, phenoxyacetic acid, benzofuran-2-carboxylic acid or 2,3-dihydrobenzofuran-2-carboxylic acid, as component B. The two components A and B can be administered separately or together as an appropriate composition or pharmaceutical preparation.

6 Claims, No Drawings

NOVEL DIURETICS

The present invention relates to novel potassium-preserving diuretics and, in particular, to pharmaceutical preparations in which the diuretic and/or saluretic action is accompanied by a comparatively limited excretion of potassium. The terms "diuretic" and "diuretic action" employed throughout this specification are to be understood as referring generally to diuretic and/or saluretic action; diuresis in the narrow sense, however, means an increased excretion of urine, and saluresis is an increased excretion of electrolytes, especially of sodium, potassium and chloride ions.

Diuretics have a broad therapeutic use. Thus they are most suitable e.g. for the treatment of cardiovascular diseases, such as congestive cardiac insufficiency. The excretion of water and electrolytes promoted by diuretics is remarkably beneficial in the medical treatment of peripheral edema, pulmonary congestion (dyspnea, orthopnea, coughing), ascites and pleural effusion. Diuretics also make possible an effective treatment of edema occurring in nephrosis and specific types of nephritis. The administration of these medicaments results in this case in an immediate excretion of retained fluid and electrolytes and affords corresponding relief to the patient. Diuretics are especially suitable for the treatment of hypertension and bring about good remedial effects in mild, moderately severe, and severe forms of this illness.

Although diuretics are often life-saving because of these beneficial therapeutic effects, most of them have the drawback that they are unspecific in respect of electrolytes, i.e. in addition to promoting the desired excretion of sodium ions they also promote the excretion of substantial amounts of potassium ions to the same extent. This loss of potassium ions results in disturbances of the heart rhythm and in muscular weakness and finds expression in a feeling of total physical exhaustion. This undesirable side-effect, which stems from electrolyte imbalance resulting from excessive potassium excretion, severely hampers the remedial action of conventional diuretics when employed in continuous therapy, e.g. in the treatment of congestive cardiac insufficiency or hypertension. For this reason attempts have been made to find physiological and therapeutic solutions which are free from these side-effects and which bring about in a warm-blooded animal, especially in man, an effective diuresis which promotes as high an excretion as possible of sodium ions while simultaneously ensuring a relatively low excretion of potassium ions.

This object is attained by the method of treatment of the present invention, which comprises the simultaneous or joint administration of an aldosterone-antagonising steroid component (component A), which consists of at least one 19-oxygenated pregnane compound, and a diuretic component which is unspecific in respect of electrolyte excretion (component B), in particular in the form of a corresponding pharmaceutical composition or of a pharmaceutical preparation.

A further object of the invention resides in the provision of pharmaceutical compositions which contain a diuretic component B which is unspecific in respect of electrolytes and the above characterised aldosterone-antagonising steroid component A, together with at least one pharmaceutical carrier or excipient. Yet a further object of the invention is to provide pharmaceutical preparations which contain a therapeutically effective amount of each of the two components A and B, in particular in the form of the above characterised pharmaceutical composition, in a dosage form.

A particular advantage of the aldosterone steroid component A resides in the complete absence of the usual sexual-specific side-effects, such as anti-androgenic action. This is of great importance in particular for continuous therapy. Exemplary of the field of use of the present invention are cardiac insufficiency, disturbances of rhythm caused by hypokalemia, pulmonary heart disease, cirrhosis of the liver, hypertension and the treatment of ascites.

The aldosterone-antagonising steroid component A consists of at least one 19-oxygenated compound of the pregnane series of the formula

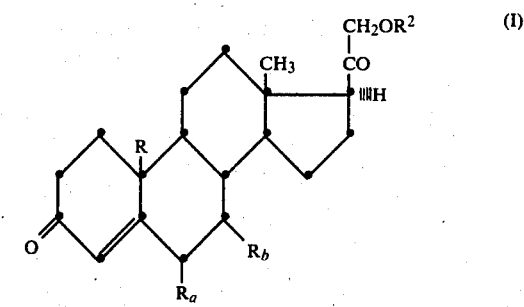

wherein
$R_a$ represents a hydrogen atom, and
$R_b$ represents an α-oriented lower alkanoylthio group, or
$R_a$ and $R_b$ together represent a carbon-carbon bond or an α- or β-oriented methylene radical,
R represents a free hydroxymethyl group or a hydroxymethyl group etherified by a lower alkyl or esterified by a lower alkanoyl; or represents a formyl group, a carboxyl group or a lower alkoxycarbonyl group, and
$R^2$ represents a hydrogen atom or the acyl radical Ac of a carboxylic acid,
and/or a corresponding salt and/or a 1,2-dehydro derivative thereof, as described in South African Pat. No. 78/3125.

These compounds are distinguished by the desired advantageous biological properties, exhibiting in animal experiments a pronounced aldosterone-antagonisting action and a reduction in the excessive retention of sodium and excretion of potassium caused by aldosterone.

Preferred aldosterone-antagonising steroids of the formula I suitable for use as component A are those which are 1,2-unsaturated and wherein $R_a$ is hydrogen, $R_b$ is α-acetylthio, R is hydroxymethyl, lower alkanoyloxymethyl, especially acetoxymethyl, or lower alkoxycarbonyl, especially methoxycarbonyl, and $R^2$ is hydrogen or lower alkanoyl, especially acetyl, in particular 7α-acetylthio-19,21-dihydroxypregn-4-en-3,20-dione or the 19-acetate, 21-acetate and 19,21-acetate thereof.

Preferred aldosterone-antagonising steroids of the formula I suitable for use as component A are also those which are 1,2-saturated and wherein $R_a$ is hydrogen, $R_b$ is α-acetylthio, R is hydroxymethyl, lower alkanoyloxymethyl, especially acetoxymethyl or lower alkoxycarbonyl, especially methoxycarbonyl, and R is hydrogen or lower alkanoyl, especially acetyl-, especially 19,21-dihydroxy-6β,7β-methylenepregn-4-en-3,20-dione, the 19-acetate, 21-acetate and 19,21-acetate thereof.

Of the compounds of the formula I above, the most preferred as component A are the aldosterone-antagonising steroids of the formula II

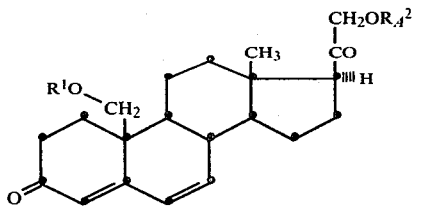

wherein $R^1$ is a lower alkanoyl radical or a hydrogen atom, and $R_A{}^2$ is an acyl radical Ac or a hydrogen atom, in particular wherein each of $R^1$ and $R_A{}^2$ is a hydrogen atom. An acyl radical Ac is preferably a lower alkanoyl radical, and a preferred lower alkanoyl radical is in turn a linear lower alkanoyl radical, in particular the acetyl radical. Compounds to be singled out for special mention are 19,21-dihydroxy-pregna-4,6-diene-3,20-dione and the 19,21-diacetate, 19-acetate and 21-acetate thereof.

Unless otherwise indicated, the expression "lower" used in connection with the definition of a compound or of a substituent, refers to a compound or a substituent containing not more than 7, preferably not more than 4, carbon atoms.

In the above-characterised formulae I and II, the acyl radical Ac is derived from the carboxylic acids customary in steroid chemistry, for example aliphatic monocarboxylic acids having 1-8 carbon atoms, such as valeric, isovaleric, trimethylacetic, hexanoic, 2,2-dimethylbutyric and heptanoic acid, and especially from straight or branched lower alkanoic acids, such as formic, propionic, butyric, isobutyric and, especially, acetic acid. However, it is also possible to use acids that are unsaturated and/or are substituted in the usual manner, for example: phenyl- and cyclohexylacetic acid, phenoxyacetic acid, 4-cyclopentylpropionic acid, haloacetic acids such as chloroacetic acid and trifluoroacetic acid, aminoacetic acid, α- or β-oxypropionic acid, benzoic acid, and aliphatic dicarboxylic acids, such as succinic and glutaric acid, or phthalic acid, the second carboxyl group of which may occur in the form of a salt, for example with an alkali metal such as potassium or sodium.

A lower alkanoylthio group is derived from the specified lower alkanoic acids and is especially the acetylthio group.

A lower alkyl radical is preferably one having a straight carbon chain, for example ethyl, propyl, butyl and especially methyl. Preferred lower alkoxy radicals correspond to the preferred lower alkyl radicals mentioned; the methoxy radical is particularly preferred.

Those compounds of the formula I which contain a free carboxyl group can also occur in the form of their salts, for example sodium, calcium, magnesium and potassium salts, or ammonium salts derived from ammonia or a suitable, preferably physiologically tolerable, organic nitrogen-containing base.

Suitable diuretic components B which are unspecific in respect of electrolyte excretion are conventional "classical" diuretics or mixtures thereof which increase diuresis both by renal and extrarenal action on tissue, in particular substances which inhibit reabsorption in the tubulus, such as saluretics or ethacrinic acid and its analogues.

Particularly suitable electrolyte-unspecific components B are benzothiadiazine derivatives, such as thiazides and hydrothiazides, benzenesulfonamides, phenoxyacetic acids, benzofuran-2-carboxylic acids and 2,3-dihydro-benzofuran-2-carboxylic acids. The electrolyte-unspecific component B can consist of a single active ingredient or of an advantageous combination of a number of active ingredients. The active ingredients can also belong to several of the above groups of compounds.

Particularly suitable thiazides are those of the formula III

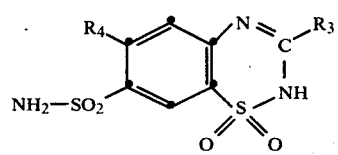

wherein $R_3$ is a hydrogen atom or a phenyl-lower alkylthio-lower alkyl group and $R_4$ is a halogen atom or the trifluoromethyl group.

A phenyl-lower alkylthio-lower alkyl radical $R_3$ is in particular one wherein each of the two lower alkyl moieties contains not more than 4 carbon atoms, in particular 1 carbon atom, and wherein the phenyl moiety is unsubstituted, e.g. the benzylthiomethyl radical.

A halogen atom $R_4$ is a bromine, iodine or fluorine atom, and in particular a chlorine atom.

Preferred compounds of the formula III are: 6-chloro-7-sulfamyl-1,2,4-benzothiadiazine 1,1-dioxide, 6-trifluoromethyl-7-sulfamyl-1,2,4-benzothiadiazine 1,1-dioxide, and 2-benzylthiomethyl-6-chloro-7-sulfamyl-1,2,4-benzothiadiazine 1,1-dioxide.

Particularly suitable hydrothiazides are those of the formula IV

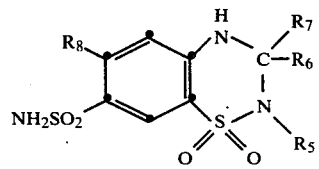

wherein $R_5$ is hydrogen or lower alkyl, $R_6$ is hydrogen, lower alkyl, lower alkenyl, cycloalkyl, cycloalkenyl, cycloalkyl-lower alkyl, aryl, aryl-lower alkyl, halo-lower alkyl, lower alkylthio-lower alkyl, lower alkenylthio-lower alkyl, halo-lower alkylthio-lower alkyl, phenyl-lower alkylthio-lower alkyl or heterocyclyl-lower alkyl, $R_7$ is hydrogen or together with $R_6$ is lower alkylene, and $R_8$ is halogen or trifluoromethyl.

A lower alkyl radical $R_5$ is one containing not more than 4 carbon atoms, such as ethyl, n-propyl, isopropyl, straight or branched butyl which is bonded in any position, and, in particular, methyl.

A lower alkyl radical $R_6$ is in particular one as defined for $R_5$, and is preferably methyl, ethyl or isobutyl.

A lower alkenyl radical $R_6$ is one containing not more than 4 carbon atoms, especially allyl.

A cycloalkyl radical $R_6$ contains 3 to 8, preferably 5 to 7, ring carbon atoms and a total of not more than 8, especially not more than 7, carbon atoms, and is e.g. cyclopentyl or cyclohexyl. A cycloalkenyl radical $R_6$ is an analogous radical containing a double bond, e.g. cyclopentenyl, cyclohexenyl or norbornenyl, especially 5-norbornen-2-yl.

A cycloalkyl-lower alkyl radical $R_6$ is one wherein the cycloalkyl moiety and the lower alkyl moiety are as defined above, and is in particular cyclopentylmethyl.

An aryl radical $R_6$ is preferably monocyclic, such as phenyl, and can be substituted by lower alkyl, such as methyl, lower alkoxy, such as methoxy, and by halogen, such as chlorine, or trifluoromethyl.

An aryl-lower alkyl radical $R_6$ is in particular one wherein both the aryl and the lower alkyl moiety are as defined above, whilst the aryl moiety is in particular unsubstituted phenyl, as in the benzyl or 1-phenylethyl radical.

A halo-lower alkyl radical $R_6$ is in particular a lower alkyl radical as defined above which carries one, two or three halogen atoms, and is preferably a halomethyl radical, e.g. trifluoromethyl, chloromethyl, dichloromethyl or trichloromethyl.

A lower alkylthio-lower alkyl radical $R_6$ is in particular one wherein both alkyl moieties are as defined above, and is preferably methylthiomethyl or 2-(methylthio)ethyl.

A lower alkenylthio-lower alkyl radical $R_6$ contains one of each of the lower alkyl and lower alkenyl radicals mentioned above, and is e.g. allylthiomethyl.

A halo-lower alkylthio-lower alkyl radical $R_6$ is in particular a radical containing one, two or three halogen atoms which is analogous to the lower alkylthio-lower alkyl radicals $R_6$ mentioned above, and is e.g. 2,2,2-trifluoroethylthiomethyl.

A phenyl-lower alkylthio-lower alkyl radical $R_6$ is in particular one wherein both alkyl moieties are as defined above, such as benzylthiomethyl.

A heterocyclyl-lower alkyl radical $R_6$ consists of a 3- to 10-membered ring, in particular a 5-membered ring, which contains one or more heteroatoms, such as a furyl or a pyrrolyl ring, and a lower alkyl radical, such as one of those specified above, in particular methyl.

A lower alkylene radical formed by $R_6$ and $R_7$ together contains not more than 6, and at least 2, in particular at least 4, carbon atoms in the alkylene chain, and is e.g. 1,5-pentylene or 3-methyl-1,5-pentylene.

A halogen atom $R_8$ is a bromine, iodine or fluorine atom, preferably a chlorine atom.

Particularly preferred compounds of the formula IV are: 3-ethyl-6-chloro-7-sulfamyl-3,4-dihydro-1,2,4-benzothiadiazine 1,1-dioxide; 3-trichloromethyl-6-chloro-7-sulfamyl-3,4-dihydro-1,2,4-benzothiadiazine-1,1-dioxide; 3-benzyl-6-trifluoromethyl-7-sulfamyl-3,4-dihydro-1,2,4-benzothiadiazine 1,1-dioxide; 2-methyl-3-(2,2,2-trifluoroethylthiomethyl)-6-chloro-7-sulfamyl-3,4-dihydro-1,2,4-benzothiadiazine 1,1-dioxide; 3-(2,2,2-trifluoroethylthiomethyl)-6-chloro-7-sulfamyl-3,4-dihydro-1,2,4-benzothiadiazine 1,1-dioxide; 3-(5-norbornen-2-yl)-6-chloro-7-sulfamyl-3,4-dihydro-1,2,4-benzothiadiazine 1,1-dioxide; 2-methyl-3-chloromethyl-6-chloro-7-sulfamyl-3,4-dihydro-1,2,4-benzothiadiazine 1,1-dioxide; 6-chloro-7-sulfamyl-3,4-dihydro-1,2,4-benzothiadiazine 1,1-dioxide; 3-dichloromethyl-6-chloro-7-sulfamyl-3,4-dihydro-1,2,4-benzothiadiazine 1,1-dioxide; 3-cyclopentylmethyl-6-chloro-7-sulfamyl-3,4-dihydro-1,2,4-benzothiadiazine 1,1-dioxide; 6-trifluoromethyl-7-sulfamyl-3,4-dihydro-1,2,4-benzothiadiazine 1,1-dioxide and 3-isobutyl-6-chloro-7-sulfamyl-3,4-dihydro-1,2,4-benzothiadiazine 1,1-dioxide.

Particularly suitable benzenesulfonamides are those of the formula

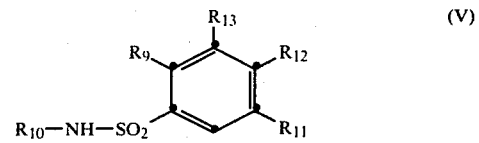

wherein $R_9$ is halogen, lower alkyl or trifluoromethyl, $R_{10}$ is hydrogen, lower alkyl, phenyl-lower alkyl, phenyl which is unsubstituted or substituted by e.g. lower alkoxy or amino, or is pyrrolidinomethyl, piperidinomethyl, piperazinomethyl, morpholinomethyl or thiomorpholinomethyl, $R_{11}$ is carboxyl, carbamoyl, N-monosubstituted or N-disubstituted sulfamoyl, lower alkylsulfonyl, or is an isoindolyl radical, and can optionally be bonded to the radical $R_{12}$; $R_{12}$ is hydrogen, lower alkyl, amino, mono- or disubstituted amino, and $R_{13}$ is hydrogen or halogen, as well as, preferably those wherein $R_9$ is phenoxy, $R_{10}$ is hydrogen, $R_{11}$ is carboxyl, $R_{12}$ is hydrogen, and $R_{13}$ is lower alkylamino, especially butylamino, or 3-(1-pyrrolyl)-propyl.

A lower alkyl radical $R_9$, $R_{10}$ or $R_{12}$ is in particular one of those specified above, preferably methyl.

An aminophenyl radical $R_{10}$ is in particular a monoaminophenyl radical, such as 4-aminophenyl.

A N-monosubstituted carbamoyl radical $R_{11}$ is in particular a N-lower alkylcarbamoyl radical, wherein lower alkyl is as defined above, and is e.g. the N-methylcarbamoyl radical. It can, however, also be N-substituted by an amino group, in which case the substituent is in particular di-lower alkylamino, such as dimethylamino, or 1-azacycloalkyl, such as pyrrolidino, piperidino or 2,6-dimethylpiperidino; the entire radical is then e.g. the N-(2,6-dimethylpiperidino)carbamoyl radical.

A N-disubstituted carbamoyl radical $R_{11}$ is in particular a N-di-lower alkylcarbamoyl radical, wherein lower alkyl is as defined above, e.g. the N,N-dimethylcarbamoyl radical.

A N-monosubstituted sulfamoyl radical $R_{11}$ is in particular a N-lower alkylsulfamoyl radical, wherein lower alkyl is as defined above, such as N-methylsulfamoyl, and also a N-furfurylsulfamoyl or N-tetrahydrofurfurylsulfamoyl radical, such as N-furfurylsulfamoyl, N-tetrahydrofurfurylsulfamoyl, N-(2-methyl-tetrahydrofurfuryl)-sulfamoyl and N-(2-methyl-4-oxo-tetrahydrofurfuryl)-sulfamoyl.

A N-disubstituted sulfamoyl radical $R_{11}$ is in particular a N,N-di-lower alkylsulfamoyl radical, wherein lower alkyl is as defined above, such as N,N-dimethylsulfamoyl, a (1-azacycloalkyl)sulfamoyl radical, wherein the 1-azacycloalkyl radical is as defined above, such as piperidinosulfonyl, a N-lower alkyl-N-carboxy-lower alkylsulfamoyl radical, wherein the lower alkyl moieties are as defined above, such as N-methyl-N-carboxymethylsulfamoyl, a N-lower alkyl-N-furfurylsulfamoyl radical, wherein lower alkyl is as defined above, such as N-methyl-N-furfurylsulfamoyl, or a N-lower alkyl-N-tetrahydrofurfurylsulfamoyl radical, wherein lower alkyl is as defined above, such as N-methyl-N-(2-methyltetrahydrofurfuryl)sulfamoyl and N-methyl-N-(2-methyl-4-oxotetrahydrofurfuryl)sulfamoyl.

A lower alkylsulfonyl radical $R_{11}$ is in particular one wherein the lower alkyl moiety is as defined above, such as methylsulfonyl, ethylsulfonyl and n-butylsulfonyl.

An isoindolinyl radical $R_{11}$ is in particular a 3-isoindolinyl radical containing a 3-hydroxy group and a 1-oxo group, such as 3-hydroxy-1-oxo-isoindolinyl-(3).

A radical $R_{11}$ bonded to a radical $R_{12}$ is in particular a carbamoyl radical $R_{11}$ which is bonded to an amino group $R_{12}$ or to a lower alkyl group $R_{12}$, such as 1-oxo-2-cyclohexyl-2-aza-propylene-(1,3) and 1-oxo-2,4-bis-aza-3-ethylbutylene-(1,4).

A monosubstituted amino group $R_{12}$ is in particular a lower alkylamino group, wherein lower alkyl is as defined above, such as methylamino, or tetrahydrofurfurylamino, or especially furfurylamino or benzylamino.

A disubstituted amino group $R_{12}$ is in particular a di-lower alkylamino group, wherein lower alkyl is as defined above, such as dimethylamino, or a di-(phenyl-lower alkyl)amino group, wherein the alkyl moiety is as defined above, such as dibenzylamino.

A halogen atom $R_{13}$ is bromine, iodine, fluorine, or especially chlorine.

Preferred compounds of the formula V are those wherein $R_9$ is chlorine, $R_{10}$ is aminophenyl, methyl or especially hydrogen, $R_{11}$ is carboxyl, carbamoyl, N-methylcarbamoyl, N-(2,6-dimethylpiperidino)carbamoyl, 3-hydroxy-1-oxo-isoindolinyl-(3) or N-methyl-N-(2-methyltetrahydrofurfuryl) sulfamoyl, or $R_{11}$ together with $R_{12}$ is 1-oxo-2-cyclohexyl-2-aza-propylene-(1,3) or 1-oxo-2,4-bis-aza-3-ethyl-butylene-(1,4), $R_{12}$ is hydrogen or furfurylamino and $R_{13}$ is hydrogen.

Especially preferred compounds of the formula V are: 2-chloro-5-N-methyl-sulfonamido-benzenesulfonamide; 2-chloro-5-N,N-dimethylsulfonamido-benzenesulfonamide; 2-chloro-5-piperidinosulfonyl-benzenesulfonamide; 2-chloro-5-(N-carboxymethyl-N-methyl)-sulfonamido-benzenesulfonamide; 2-chloro-5-(N-furfuryl-sulfonamido)-benzenesulfonamide; 2-chloro-5-(N-tetrahydrofurfuryl-sulfonamido)-benzenesulfonamide; 2-chloro-5-[N-methyl-N-(2-methyl-4-oxo-tetrahydrofurfuryl)-sulfonamido]-benzenesulfonamide; 4,5-dichlorobenzene-1,3-disulfonamide; 4-chloro-6-methylbenzene-1,3-disulfonamide; 4-chloro-6-aminobenzene-1,3-disulfonamide; 2-chloro-5-methylsulfonylbenzenesulfonamide; 2-chloro-5-ethylsulfonylbenzenesulfonamide; 2-chloro-5-n-butylsulfonyl-benzenesulfonamide; 2-methyl-5-ethylsulfonylbenzenesulfonamide; 2-methyl-5-methylsulfonyl-benzenesulfonamide; 2-methyl-5-n-butylsulfonyl-benzenesulfonamide; 2-chloro-4-(N,N-dibenzylamino)-5-carboxyl-benzenesulfonamide; 2-furfurylamino-4-chloro-5-N-(p-aminophenyl)-sulfamoyl-benzoic acid, 2-furfurylamino-4-chloro-5-N-(O-aminophenyl)-sulfamoylbenzoic acid and especially 3-sulfonamido-4-chlorobenzoic acid; 3-sulfonamido-4-chlorobenzamide; 3-(N-methylsulfamoyl)-4-chloro-N-methylbenzamide; 1-chloro-4-[N-methyl-N-(2-methyltetrahydrofurfuryl)-sulfamoyl]benzenesulfonamide; 1,3-disulfamoyl-4-chlorobenzene; 2-chloro-5-[3-hydroxy-1-oxoisoindolyl-(3)]-benzenesulfonamide; 2-ethyl-4-oxo-6-sulfamoyl-7-chloro-1,2,3,4-tetrahydro-quinazoline; 1-oxo-2-cyclohexyl-5-chloro-6-sulfamoyl-1,2-dihydroisoindole; 2-chloro-5-[N-(2,6-dimethylpiperidino)-carbamoyl]-benzenesulfonamide; 2-chloro-4-furfurylamino-5-carboxyl-benzenesulfonamide and 2-chloro-4-benzylamino-5-carboxyl-benzenesulfonamide.

Particularly suitable phenoxyacetic acids are those of the formula

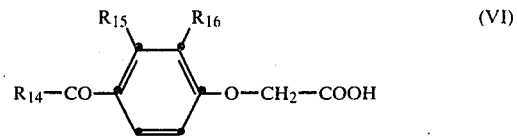

(VI)

wherein $R_{14}$ is furyl, thienyl, lower alkylthienyl or 1-lower alkylvinyl, $R_{15}$ is halogen or lower alkyl and $R_{16}$ is hydrogen, halogen or lower alkyl, or $R_{15}$ and $R_{16}$ together are the radical of a fused benzene ring, i.e. 1,3-butadienylene-1,4.

The lower alkyl moiety of 1-lower alkylvinyl contains preferably 2 to 7, especially 2 to 4, carbon atoms, and is preferably unbranched. Accordingly, it forms 1-propylvinyl, 1-butylvinyl and, in particular, 1-ethylvinyl.

A halogen atom $R_{15}$ or $R_{16}$ is bromine, iodine or fluorine and preferably chlorine, especially if $R_{14}$ is one of the heterocyclyl radicals specified above.

A lower alkyl radical $R_{15}$ or $R_{16}$ is in particular one which contains not more than 4 carbon atoms, preferably methyl.

Phenoxyacetic acids are also compounds of the formula VIA

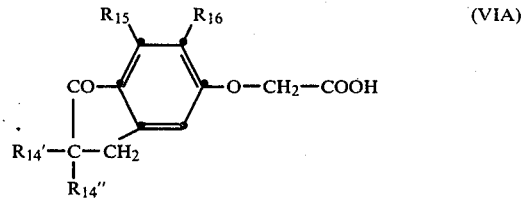

(VIA)

wherein $R_{15}$ and $R_{16}$ have the given meanings and are especially chlorine or methyl, $R_{14}'$ is lower alkyl containing not more than 3 carbon atoms, especially methyl, and $R_{14}''$ is lower alkyl containing not more than 3 carbon atoms, phenyl, p-chlorophenyl or thienyl.

Particularly suitable compounds of the formula VI or VIA are:

(a) [2,3-dimethyl-4-(2-methylenebutyryl)-phenoxy] acetic acid, [2-methyl-3-chloro-4-(2-methylenebutyryl)-phenoxy] acetic acid, [4-(2-methylenebutyryl)-1-naphthoxy] acetic acid and especially [2,3-dichloro-4-(2-methylenebutyryl)-phenoxy] acetic acid.

(b) 4-thenoyl-2,3-dichlorophenoxy acetic acid, 4-(5-methylthenoyl)-2,3-dichlorophenoxy acetic acid and 4-furoyl-2,3-dichlorophenoxy acetic acid; and (c) (1-oxo-2-methyl-2-phenyl-6,7-dichloro-5-indanyloxy) acetic acid (especially as racemate or the laevo-form), or also [1-oxo-2-(4-chlorophenyl)-6,7-dichloro-5-indanyloxy] acetic acid and [1-oxo-2-(2-thienyl)-6,7-dichloro-5-indanyloxy] acetic acid.

Particularly suitable benzofuran-2-carboxylic acids are those of the formula VII

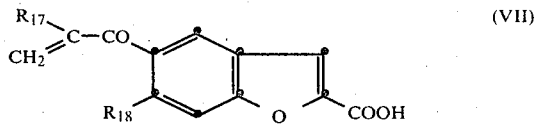

(VII)

wherein $R_{17}$ is lower alkyl and $R_{18}$ is lower alkyl or lower alkoxy.

A lower alkyl radical $R_{17}$ is in particular one containing 2 to 7, preferably 2 to 4, carbon atoms, such as one of those specified above, and is preferably unbranched, such as ethyl.

A lower alkyl radical $R_{18}$ is in particular one containing not more than 4 carbon atoms, preferably methyl.

A lower alkoxy radical $R_{18}$ is in particular one wherein the alkyl moiety contains not more than 4 carbon atoms, preferably methoxy.

Suitable compounds of the formula VII are in particular: 5-(2-methylenebutyryl)-6-methyl-benzofuran-2-carboxylic acid, 5-(2-methylenebutyryl)-6-methoxy-benzofuran-2-carboxylic acid and 5-(2-methylenepropionyl)-6-methylbenzofuran-2-carboxylic acid.

Particularly suitable 2,3-dihydrobenzofuran-2-carboxylic acids are those of the formula VIII

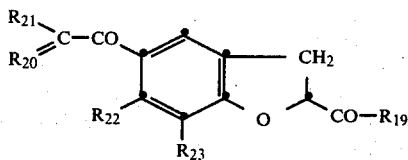

(VIII)

wherein $R_{19}$ is hydroxyl, alkoxy, cycloalkoxy or aralkoxy, $R_{20}$ is two hydrogen atoms or lower alkylidene, $R_{21}$ is lower alkyl, $R_{22}$ is hydrogen, halogen, lower alkyl or lower alkoxy, and $R_{23}$ is hydrogen or lower alkyl.

An alkoxy radical $R_{19}$ is in particular one containing 1 to 18, especially 1 to 12, carbon atoms, such as methoxy, ethoxy, n-butoxy, 2-hexyloxy and n-decyloxy.

A cycloalkoxy radical $R_{19}$ is in particular one containing 3 to 8, preferably 5 to 7, ring carbon atoms, and preferably not more than 10, most preferably not more than 8, carbon atoms, and is cyclopentyloxy or cyclohexyloxy.

An aralkoxy radical $R_{19}$ is in particular phenyl-lower alkoxy the lower alkyl moiety of which contains not more than 4 carbon atoms, and is preferably benzyloxy.

A lower alkylidene radical $R_{20}$ is in particular one containing not more than 4 carbon atoms and is preferably methylene or ethylidene.

A lower alkyl radical $R_{21}$ is one containing in particular not more than 4 carbon atoms and is preferably straight-chain, such as methyl, n-propyl, n-butyl and especially ethyl.

A halogen atom $R_{22}$ can be bromine or iodine, but is preferably fluorine and most preferably chlorine.

A lower alkyl radical $R_{22}$ or $R_{23}$ is one containing in particular not more than 4 carbon atoms, such as one of those specified above, preferably methyl.

A lower alkoxy radical $R_{22}$ is in particular one containing not more than 4 carbon atoms, such as one of those specified above, preferably methoxy.

Preferred compounds of the formula VIII are those wherein $R_{19}$ is hydroxyl, $R_{20}$ is methylene or ethylidene, $R_{21}$ is straight-chain alkyl of 1 to 4 carbon atoms, $R_{22}$ is methyl, methoxy, chlorine or fluorine, and $R_{23}$ is hydrogen or methyl.

Especially preferred compounds of the formula VIII are: 5-(2-methylenebutyryl)-6-methyl-2,3-dihydrobenzofuran-2-carboxylic acid; 5-(2-methylenebutyryl)-6-fluoro-2,3-dihydro-benzofuran-2-carboxylic acid; 5-(2-methylenebutyryl)-6-chloro-2,3-dihydro-benzofuran-2-carboxylic acid; 5-(2-methylenepropionyl)-6-methyl-2,3-dihydro-benzofuran-2-carboxylic acid; 5-(2-methylenehexanoyl)-6-methyl-2,3-dihydro-benzofuran-2-carboxylic acid; 5-(2-methylenevaleryl)-6-methyl-2,3-dihydrobenzofuran-2-carboxylic acid; 5-(2-methylenepropionyl)-6-methyl-2,3-dihydro-benzofuran-2-carboxylic acid; 5-(2-ethylidene-butyryl)-6-methyl-2,3-dihydro-benzofuran-2-carboxylic acid; 5-(2-methylenebutyryl)-6-methyl-2,3-dihydro-benzofuran-2-carboxylic acid methyl ester; 5-(2-methylenebutyryl)-6-methyl-2,3-dihydrobenzofuran-2-carboxylic acid ethyl ester; 5-(2-methylenebutyryl)-6-methyl-2,3-dihydro-benzofuran-2-carboxylic acid n-butyl ester; 5-(2-methylenebutyryl)-6-methyl-2,3-dihydro-benzofuran-2-carboxylic acid 2-hexyl ester; 5-(2-methylenebutyryl)-6-methyl-2,3-dihydro-benzofuran-2-carboxylic acid n-decyl ester; 5-(2-methylenebutyryl)-6-methyl-2,3-dihydro-benzofuran-2-carboxylic acid cyclopentyl ester; 5-(2-methylenebutyryl)-6-methyl-2,3-dihydrobenzofuran-2-carboxylic acid cyclohexyl ester; 5-(2-methylenebutyryl)-6-methyl-2,3-dihydro-benzofuran-2-carboxylic acid benzyl ester; 5-(2-methylenebutyryl)-7-methyl-2,3-dihydro-benzofuran-2-carboxylic acid methyl ester; 5-(2-methylenebutyryl)-6-chloro-7-methyl-2,3-dihydro-benzofuran-2-carboxylic acid methyl ester; 5-(2-methylenepropionyl)-6-methyl-2,3-dihydro-benzofuran-2-carboxylic acid methyl ester; 5-(2-methylenevaleryl)-6-methyl-2,3-dihydro-benzofuran-2-carboxylic acid methyl ester; 5-(2-methylene-3-methyl-butyryl)-6-methyl-2,3-dihydro-benzofuran-2-carboxylic acid methyl ester; and 5-(2-methylenebutyryl)-6-fluoro-2,3-dihydro-benzofuran-2-carboxylic acid methyl ester, and especially 5-(2-methylenebutyryl)-6,7-dimethyl-2,3-dihydro-benzofuran-2-carbonoxylic acid; 5-(2-methylene-3-methyl-butyryl)-6-methyl-2,3-dihydrobenzofuran-2-carboxylic acid, 5-(2-methylenebutyryl)-6-chloro-7-methyl-2,3-dihydro-benzofuran-2-carboxylic acid.

Depending on the number of asymmetrical carbon atoms they contain, the diuretics of the above formulae III to VIII can be obtained in the form of mixtures of isomers, pure isomers (racemates) or optical antipodes. Preferably they are employed in the form of the respective more active and less toxic isomer or antipode.

The diuretics of the formulae III to V containing basic groups can be both in the free form and in the form of their non-toxic salts. Such salts are in particular salts with organic or inorganic acids, e.g.: hydrohalic acid, sulfuric acids, phosphoric acids, nitric acid, perchloric acid, aliphatic, alicyclic, aromatic or heterocyclic carboxylic or sulfonic acids, such as formic, acetic, propionic, succinic, glycolic, lactic, malic, tartaric, citric, ascorbic, maleic, hydroxymaleic or pyruvic acid; phenylacetic, benzoic, p-aminobenzoic, anthranilic, p-hydroxybenzoic, salicylic or p-aminosalicylic acid, methanesulfonic, ethanesulfonic, hydroxyethanesulfonic, toluenesulfonic, naphthalenesulfonic or sulfanilic acid; cyclohexylsulfamic acid, methionine, tryptophane, lysine or arginine.

The diuretics containing acid groups of the formulae VI to VIII can also be in the free form or in the form of their non-toxic salts. Such salts are in particular the salts with bases as mentioned at the outset in respect of the compounds of the formula I. Aluminium salts, e.g. salts of 2 moles of acid and 1 mole of aluminium hydroxide, are also suitable, especially owing to their slower absorption, odourlessness and low gastrointestinal irritability.

The invention also relates to methods of obtaining the compositions and pharmaceutical preparations of the invention, and to the use of the combination of active ingredients A and B both in the form of the said compositions and pharmaceutical preparations and of a method of treating pathological conditions which are consequent on the impaired excretion of urine and urinary constituents, especially water and electrolytes, said method comprising the combined or separate administration of both active ingredients.

Especially advantageous compositions and pharmaceutical preparations are those containing the active ingredients of the formulae I to VIII singled out for special mention above as being preferred, e.g. 19,21-dihydroxypregna-4,6-diene-3,20-dione, the 19,21-diacetate, 19-monoacetate or 21-monoacetate thereof, as component A, and, as the diuretic component B which is unspecific in respect of electrolytes, 1-oxo-3-(3-sulfamyl-4-chlorophenyl)-3-hydroxyisoindoline, 6-chloro-7-sulfamyl-3,4-dihydro-1,2,4-benzothiadiazine 1,1-dioxide, 3-cyclopentylmethyl-6-chloro-7-sulfamyl-3,4-dihydro-1,2,4-benzothiadiazine 1,1-dioxide, 4-(2-methylenebutyryl)-2,3-dichlorophenoxyacetic acid, 4-thenoyl-2,3-dichlorophenoxyacetic acid, 1-oxo-2-methyl-2-phenyl-6,7-dichloro-5-indanyloxyacetic acid, 2-chloro-4-furfurylamino-5-carboxybenzenesulfonamide, 2-phenoxy-3-butylamino-5-carboxybenzenesulfonamide or 2-phenoxy-3-[3-(pyrrolyl)-propyl]-5-carboxybenzenesulfonamide.

In the compositions and pharmaceutical preparations of this invention, the ratio of component A to component B, based on the respective average effective dose, is about 4:1 to about 1:4, preferably from about 3:2 to about 2:3. As the average effective dose of each specific component is a value obtainable by known pharmacological test methods, it is easily possible for the skilled person to prescribe, within the above limits, a suitable ratio of both components for each patient in accordance with the specific complaint, general state of health, individual tolerance and age, and species. It will also be understood that the size of the dosage units of the medicaments of the invention depends primarily on the potency of the respective component A and B as preferably expressed by the daily dose.

The term "dosage units" is used in this connection to mean individual separate portions of homogeneous compositions which are suitable for medicinal administration and which each contains a specific amount of the active ingredient of the invention corresponding to about 0.05 to about 2, preferably about 0.15 to about 1, daily dose.

Thus, for example, the especially preferred preparations referred to above can contain, per dosage unit, 15 to 150 mg, in particular 20 to 100 mg, of 19,21-dihydroxy-4,6-diene-3,20-dione or one of its acetates, as component A. The content of component B is e.g. 10 to 100 mg, especially 25 to 50 mg, of 2-chloro-5-[3-hydroxy-1-oxo-isoindolyl-(3)]-benzenesulfonamide, or 4-(2-methylenebutyryl)-2,3-dichlorophenoxyacetic acid, 5 to 50 mg, especially 12 to 25 mg, of 6-chloro-7-sulfamyl-3,4-dihydro-1,2,4-benzothiadiazine 1,1-dioxide or 2-chloro-4-furfurylamino-5-carboxybenzenesulfonamide, 0.1 to 1.0 mg especially 0.25 to 0.5 mg, of 3-cyclopentylmethyl-6-chloro-7-sulfamyl-3,4-dihydro-1,2,4-benzothiadiazine 1,1-dioxide or 2-phenoxy-3-butylamino-5-carboxybenzenesulfonamide, 2 to 20 mg, especially 5 to 10 mg, of 2-phenoxy-3-[3-(1-pyrrolyl)-propyl]-5-carboxybenzenesulfonamide, 100 to 400 mg, especially 200 mg, of 4-thenoyl-2,3-dichloro-phenoxyacetic acid, and 5 to 25 mg, especially 10 mg, of racemic (1-oxo-2-methyl-2-phenyl-6,7-dichloro-5-indanyloxy)-acetic acid, or half the amount of the L-form of this acid.

For the treatment of an edema of medium severity, a daily dosage of 1-3 dosage units is recommended, which units contain the active substances amounting to the upper limits of the respective especially preferred amounts outlined above; a case of medium severity of an essential hypertension can be treated, e.g. with a daily dosage of 1-3 dosage units, containing the active substances in amounts of the lower especially preferred limits.

Throughout this specification, the term "active ingredient" denotes in particular a compound of the formulae I to VIII as defined in connection with the compositions and pharmaceutical preparations of this invention by the general and, in particular, specific meanings given herein. The term "composition" refers to mixtures of active ingredients of both types, optionally together with suitable carriers and excipients in a desired arithmetically determined ratio, and which are obtained by conventional pharmaceutical methods. The term "pharmaceutical preparation" refers to individual separate portions of homogeneous composition which are suitable for medicinal administration.

As has already been stated above, the invention relates to pharmaceutical preparations, especially to pharmaceutical preparations in dosage unit form, preferably in solid form, containing at least one 19-oxygenated pregnane compound of the formula I as aldosterone-antagonising component A, and at least one electrolyte-unspecific diuretic as component B, optionally together with at least one pharmaceutical carrier or excipient. The invention relates in particular to medicaments in the form of tablets (including lozenges, granules and pastilles), sugar-coated tablets, capsules, pills or suppositories, containing both components A and B with or without the admixture of one or more excipients.

The pharmaceutical compositions preferably contain about 0.1 to about 99.5%, especially from about 1 to about 90%, by weight of the active ingredient mixture.

The pharmaceutical compositions and preparations of the invention are intended especially for enteral, most preferably oral or rectal, application. Preferably they are in the form of tablets, sugar-coated tablets or, less preferably, suppositories or capsules, which, in addition to containing the active ingredients to be used according to the invention, contain the excipients and carriers customarily employed for the respective formulation and which assist the incorporation of the active ingredient into the desired formulation and make possible a controlled release of the active ingredients. The pharmaceutical preparations of this invention can also be formulated as inlay tablets or sugar-coated inlay tablets. These consist basically of a tablet or sugar-coated tablet core which contains one component, an "inlay" which contains the other component and which is compressed into the core, and, if required, conventional separating, covering and/or protective layers.

The core is preferably composed of the cited active ingredient or an active ingredient/excipient mixture which contains it and, if desired, excipients, carriers and/or coating substances.

An active ingredient/excipient mixture consists for example of corresponding granules which are suitable for processing to tablets, sugar-coated tablets or capsules. In addition to the active ingredient, such granules contain, inter alia, diluents or fillers, such as sugar, for example lactose or saccharose, or sugar alcohols, for example mannitol or sorbitol, cellulose preparations and/or calcium phosphates, for example tricalcium phosphate or calcium hydrogen phosphate, as well as glidants, such as talc or colloidal silicic acid, lubricants, such as stearic acid or salts thereof, for example magnesium or calcium stearate, and/or polyethylene glycol, and also glycerides, such as hydrogenated cotton seed oil or hydrogenated castor oil.

Granules of this kind can be prepared in a manner which is known per se, with or without the use of moistening agents, such as water or organic solvents, for example ethanol, or mixtures thereof.

The pharmaceutical preparations of the present invention are obtained in a manner known per se, e.g. by conventional mixing, granulating, sugar-coating, solution or lyophilising methods. Accordingly, tablet and sugar-coated tablet cores for oral administration can be obtained by combining the active ingredients with solid carriers, if desired granulating the resulting mixture and processing the mixture or granulate, if desired or necessary after the addition of suitable excipients, to tablets or sugar-coated tablet cores.

Suitable carriers are e.g. sugar, for example, lactose, saccharose, mannitol or sorbitol, conventional cellulose preparations, calcium phosphates, e.g. tricalcium phosphate or calcium hydrogen phosphate, binders such as starch pastes, for example maize, corn, rice or potato starch paste, gelatin, tragacanth, methyl cellulose, sodium carboxymethylcellulose and/or polyvinylpyrrolidone, also carboxymethyl starch, crosslinked polyvinylpyrrolidone, agar, alginic acid or a salt thereof, such as sodium alginate, and/or, if desired, disintegrators, such as the above starches. Excipients are chiefly glidants and lubricants, for example, silicic acid, talc, stearic acid or salts thereof, such as magnesium stearate or calcium stearate, and/or polyethylene glycol. Sugar-coated tablet cores are provided with suitable coatings that can be resistant to gastric juices, using, inter alia, concentrated sugar solutions which may contain gum arabic, talc, polyvinylpyrrolidone, polyethylene glycol and/or titanium dioxide, shellac solutions in suitable organic solvents or solvent mixtures or, for the preparation of coatings resistant to gastric juices, solutions of suitable cellulose preparations, such as acetylcellulose phthalate or hydroxypropylmethylcellulose phthalate. The duration of effect of an intrinsically short-acting active ingredient can be prolonged for example by incorporating it in a suitable carrier which effects its slow release. This is especially the case if one of the two components, e.g. component A, has a markedly shorter duration of action than the other. The component having the shorter duration of action is then incorporated in a delayed release core and the longer acting component is incorporated in the covering layer. Dyes or pigments can be added to the tablets or sugar-coated tablet cores, for example to identify or indicate different doses of active ingredient.

Further pharmaceutical preparations for oral administration are dry-filled capsules, and also soft sealed capsules made from gelatin and a plasticiser, such as glycerin or sorbitol. The dry-filled capsules can contain the active ingredient in the form of granules, for example of those described in more detail hereinafter. In soft capsules, the active ingredient is preferably dissolved or suspended in suitable liquids, for example in fatty oils, paraffin oil or liquid polyethylene glycols, to which stabilisers can also be added.

Pharmaceutical preparations suitable for rectal administration are e.g. suppositories, which consist in principle of a combination of the active ingredients with a suppository base. Examples of suitable suppository bases are natural or synthetic triglycerides, paraffin hydrocarbons, polyethylene glycols or higher alkanols. It is furthermore also possible to use gelatin rectal capsules which consist of a combination of the active ingredients with a base material. Examples of suitable base materials are liquid triglycerides and polyethylene glycols.

As explained above, the pharmaceutical preparations of this invention for enteral, preferably oral, administration are obtained in a manner known per se. The following Examples described their manufacture in more detail.

EXAMPLE 1

Tablets containing about 100 mg of component A and about 25 mg of component B are manufactured as follows:

| Composition of one tablet: | |
|---|---|
| component A, micronised | 100.0 mg |
| component B, micronised | 25,0 mg |
| corn starch | 50.0 mg |
| colloidal silica | 5,0 mg |
| gelatin | 5.0 mg |
| microcrystalline cellulose | 75.0 mg |
| sodium carboxymethyl starch | 20.0 mg |
| magnesium stearate | 1.5 mg |
| | 381.5 mg. |

Manufacture of 100.000 tablets 10 kg of micronised component A, 2.5 kg of micronised component B and 0.5 kg of corn starch are mixed with 0.5 kg of colloidal silica and worked into a moist composition with a solution of 0.5 kg of gelatin in 5.0 kg of distilled water (30° C.). This mixture is forced through a sieve having a mesh width of 3 mm and dried at 45° C. (fluidised bed drier). The dry granulate is pressed through a sieve having a mesh width of 0.8 mm, mixed with a previously sieved mixture of 7.5 kg of microcrystalline cellulose and 2.0 kg of sodium carboxymethyl starch and with 0.15 kg of magnesium stearate and compressed to tablets weighing 381.5 mg.

Component A is 19,21-dihydroxypregna-4,6-diene-3,20-dione-19,21-diacetate, and component B is 6-chloro-7-sulfamyl-3,4-dihydro-1,2,4-benzothiadiazine 1,1-dioxide.

The following active ingredients can be used in analogous manner in the corresponding proportions:

component A: 19,21-dihydroxypregna-4,6-diene-3,20-dione, the 19-acetate or 21-acetate thereof (100 mg each)

component B: 2-chloro-5-(3-hydroxy-1-oxo-isoindolyl-3)-benzenesulfonamide (50 mg), 4-(2-methylenebutyryl)-2,3-dichlorophenoxyacetic acid (50 mg), racemic (1-oxo-2-methyl-2-phenyl-6,7-dichloroindanyl-5-oxy)-acetic acid (20 mg, or 10 mg of the L-form), or 3-cyclopentylmethyl-6-chloro-7-sulfamyl-3,4-dihydro-1,2,4-benzothiadiazine 1,1-dioxide (0.5 mg).

EXAMPLE 2

Sugar-coated tablets containing about 100 mg of component A and 20 mg of component B are manufactured as follows:

| Composition of a sugar-coated tablet core: | |
| --- | --- |
| component A, micronised | 100.0 mg |
| component B, micronised | 20.0 mg |
| corn starch | 90.0 mg |
| tricalcium phosphate | 90.0 mg |
| polyvinylpyrrolidone K 25 | 15.0 mg |
| magnesium stearate | 2.0 mg |
| sodium carboxymethylcellulose | 33.0 mg |
| | 350.0 mg |

Manufacture of 50.000 sugar-coated tablet cores

A mixture of 5 kg of component A, 1.0 kg of component B, 4.5 kg of corn starch and 5 kg of tricalcium phosphate is granulated with a solution of 0.75 kg of polyvinylpyrrolidone K 25 in 5 kg of distilled water in a fluidised bed process. The granulate is dried at 45° C. and pressed through a sieve having a mesh width of 1 mm, then mixed with 0.1 kg of magnesium stearate and 1.65 kg of sodium carboxymethyl starch. The mixture is compressed to 350 mg domed tablets.

Manufacture of 6.6 kg of sugar-coated tablets 6 kg of the sugar-coated tablet cores are coated in portions in a coating pan of 45 cm diameter with a sugar syrup (2 parts sugar and 1 part by weight of distilled water), in which 1.5% polyvinylpyrrolidone K 25 and 1% polyethylene glycol 6000 are dissolved and 20% of talc is suspended, until each tablet has a weight of 410 mg, while drying with warm air of approximately 60°. Subsequently sugar syrup (2 parts of sugar and 1 part of water) is applied in portions until the tablets have a final weight of 450 mg. The sugar-coated tablets are finally glazed with a solution of 2% carnauba wax in trichloroethylene.

Component A: 19,21-dihydroxypregna-4,6-diene-3,20-dione-19,21-diacetate.

Component B: 2-chloro-4-furfurylamino-5-carboxybenzenesulfonamide.

The following active ingredients can also be used in the corresponding proportions:

component A: 19,21-dihydroxypregna-4,6-diene-3,20-dione, the 19-acetate or 21-acetate thereof (100 mg each);

component B: 2-chloro-5-(3-hydroxy-1-oxo-isoindolyl-3)-benzenesulfonamide (50 mg), 4-(2-methylenebutyryl)-2,3-dichlorophenoxyacetic acid (50 mg), 6-chloro-7-sulfamyl-3,4-dihydro-1,2,4-benzothiadiazine 1,1-dioxide (25 mg) or 2-phenoxy-3-butylamino-5-carboxybenzenesulfonamide (0.5 mg).

EXAMPLE 3

Soft gelatin capsules containing 50 mg of component A and 12.5 mg of component B are obtained as follows:

| Composition of a soft gelatin capsule: | |
| --- | --- |
| component A, micronised | 50.0 mg |
| component B, micronised | 12.5 mg |
| soya lecithin | 1.5 mg |
| beeswax | 2.5 mg |

| Composition of a soft gelatin capsule: | |
| --- | --- |
| vegetable oil | 100.0 mg |
| vegetable oil, partially hydrogenated | 54.0 mg |
| | 220.5 mg |

Manufacture of 100,000 soft gelatin capsules 6.25 kg of an intimate mixture of micronised components A and B (4:1 by weight) is suspended in a mixture, produced by melting, of 0.15 kg of soya lecithin, 0.25 kg of beeswax, 5.4 kg of partially hydrogenated vegetable oil and 10 kg of vegetable oil and the resultant mass is made into gelatin capsules by a stamping process. The gelatin casing consists of about 71% of gelatin, about 28% of glycerin (85%) and about 1% of titanium dioxide as well as 0.3% of p-hydroxybenzoic acid propyl ester. The size of the capsule is 4 minims (oblong shape).

Component A: 19,21-dihydroxypregna-4,6-diene-3,20-dione,

Component B: 6-chloro-7-sulfamyl-3,4-dihydro-1,2,4-benzothiadiazine 1,1-dioxide.

The following active ingredients can also be used in the respective amounts:

component A: 19,21-dihydroxypregna-4,6-diene-3,20-dione-19-acetate, -21-acetate or -19,21-acetate (50 mg each)

component B: 2-chloro-5-(3-hydroxy-1-oxo-isoindolyl-3)-benzenesulfonamide (25 mg), 2-chloro-4-furfurylamino-5-carboxybenzenesulfonamide (15 mg), 4-thienyl-2,3-dichlorophenoxyacetic acid (125 mg) or 3-cyclopentylmethyl-6-chloro-7-sulfamyl-3,4-dihydro-1,2,4-benzothiadiazine 1,1-dioxide (0.25 mg).

EXAMPLE 4

Film-coated tablets containing 100 mg of component A and 10 mg of component B are obtained as follows:

| Composition of a film-coated tablet core: | |
| --- | --- |
| component A, micronised | 100.0 mg |
| component B, micronised | 10.0 mg |
| polyethylene glycol 6000 | 52.0 mg |
| colloidal silica | 5.0 mg |
| stearic acid | 3.0 mg |
| | 170.0 mg |

Production of 10.000 cores 1.10 kg of an intimate mixture of micronised active components A and B (10:1 by weight) is mixed with a melt of 0.52 kg of polyethylene glycol [prepared with the addition of 0.05 kg of colloidal silica (specific surface area of 200 m$^2$/g)] and after cooling the mixture is pressed through a sieve having a mesh width of 1 mm. Then 0.03 kg of pulverulent, previously sieved stearic acid is admixed with the granulate and the mixture is compressed to 160 mg slightly domed tablets.

Production of 30.000 film-coated tablets 4.8 kg of cores are continuously sprayed in a coating pan of 45 cm diameter, while introducing air of 35° C., with a solution of hydroxypropylmethylcellulose (viscosity 6 cP, 2% solution in water) in distilled water, in which 2% talc is suspended, until there is 5 mg of coating on each core.

Component A: 19,21-dihydroxypregna-4,6-diene-3,20-dione

Component B: 2-phenoxy-3-[3-(1-pyrrolyl)-propyl]-5-carboxybenzenesulfonamide.

The following active ingredients can also be used in the respective amounts:

component A: 19,21-dihydroxypregna-4,6-diene-3,20-dione-19-acetate, -21-acetate or -19,21-diacetate (50 mg each)

component B: 6-chloro-7-sulfamyl-3,4-dihydro-1,2,4-benzothiadiazine 1,1-dioxide (25 mg), 2-chloro-5-(3-hydroxy-1-oxo-isoindolyl-3)-benzenesulfonamide (50 mg), 4-(2-methylenebutyryl)-2,3-dichlorophenoxyacetic acid (50 mg), 2-chloro-4-furfurylamino-5-carboxybenzenesulfonamide (20 mg), 2-phenoxy-4-butylamino-5-carboxybenzenesulfonamide (0.5 mg) or 3-cyclopentylmethyl-6-chloro-7-sulfamyl-3,4-dihydro-1,2,4-benzothiadiazine 1,1-dioxide (0.5 mg).

EXAMPLE 5

Sugar-coated tablets containing 40 mg of 19,21-dihydroxypregna-4,6-diene-3,20-dione as component A and 10 mg of 6-chloro-7-sulfamyl-3,4,-dihydro-1,2,4-benzothiadiazine 1,1-dioxide as component B.

| Composition of a sugar-coated tablet Core: | |
| --- | --- |
| 19,21-dihydroxy-pregna-4,6-diene-3,20-dione | 40 mg |
| lactose | 160 mg |
| stearyl alcohol | 77 mg |
| polyvinylpyrrolidone | 20 mg |
| magnesium stearate | 3 mg |
| | 300 mg |
| Protective coating Shell: | |
| 6-chloro-7-sulfamyl-3,4-dihydro-1,2,4-benzo thiadiazine-1,1-dioxide | 10 mg |
| sugar, talc, colourant | 190 mg |
| binder q.s. ad | |
| | 500 mg |

Manufacture

The steroid component and lactose are granulated with the stearyl alcohol melt and a concentrated polyvinyl pyrrolidone solution and the granulate is dried. The resultant mass is sieved and compressed to vaulted tablets of 300 mg. These tablets are provided with a protective coating and are then coated with coloured sugar syrup, in which the diuretic component is dissolved, to a final weight of about 500 mg.

EXAMPLE 6

Gelatin capsules containing about 50 mg of 19,21-dihydroxypregna-4,6-diene-3,20-dione as component A and 125 mg of 4-thenoyl-2,3-dichlorophenoxyacetic acid as component B are prepared as follows:

| Composition of a dry-filled capsule | |
| --- | --- |
| 19,21-dihydroxypregna-4,6-diene-3,20-dione | 50.0 mg |
| 4-thenoyl-2,3-dichlorophenoxyacetic acid | 125.0 mg |
| lactose | 124.0 mg |
| magnesium stearate | 1.0 mg |
| | 350.0 mg |

Manufacture of 100,000 dry-filled capsules 0.50 kg of very finely ground 19,21-dihydroxypregna-4,6-diene-3,20-dione is intimately mixed with 1.25 kg of 4-thenoyl-2,3-dichlorophenoxyacetic acid and, if necessary, this mixture is further comminuted. To this mixture are added 1.24 kg of very finely ground lactose and 0.01 kg magnesium stearate through a sieve and the mixture is homogenised. The powder is sieved and packed into 350 mg gelatin capsules.

The other active ingredients mentioned in the description of this specification can be formulated to analogous pharmaceutical preparations as illustrated in the foregoing Examples 1 to 6.

What is claimed is:

1. A diuretic, petassium-preserving pharmaceutical composition comprising (A) an aldosterone antagonising amount of at least one 19-oxygenated pregane of the formula

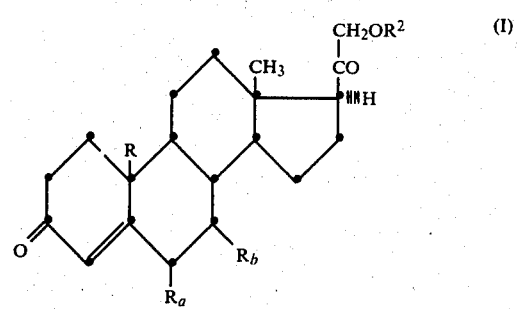

wherein $R_a$ is a hydrogen atom, and $R_b$ is an α-oriented lower alkanoylthio group, or $R_a$ and $R_b$ together are a carbon-carbon bond or an α- or β-oriented methylene radical, R is a free hydroxymethyl group or a hydroxymethyl group etherified by a lower alkyl or esterified by a lower alkanoyl; or is a formyl group, a carboxyl group or a lower alkoxy-carbonyl group, and $R^2$ is a hydrogen atom or the acyl radical of a carboxylic acid, or a salt or a 1,2-dehydro derivative thereof; (B) a diuretically effective amount of at least one diuretic selected from the group consisting of the benzothiadiazine; dihydrobenzothiadiazine, benzenesulfonamide, phenoxyacetic acid, benzofuran-2-carboxylic acid and 2,3-dihydrobenzofuran-2-carboxylic acid series; and (C) a pharmaceutical excipient.

2. A composition according to claim 1, which contains the components A and B in dosage unit form.

3. A composition according to claim 1, wherein component A is the 19,21-dihydroxypregna-4,6-diene-3,20-dione; or the 19,21-diacetate, 19-acetate or 21-acetate thereof.

4. A composition according to claim 1, wherein component B is 1-oxo-3-(3-sulfamyl-4-chlorophenyl)-3-hydroxyisoindoline, 6-chloro-7-sulfamyl-3,4-dihydro-1,2,4-benzothiadiazine 1,1-dioxide, 3-cyclopentylmethyl-6-chloro-7-sulfamyl-3,4-dihydro-1,2,4-benzothiadiazine 1,1-dioxide, 4-(2-methylenebutyryl)-2,3-dichlorophenoxyacetic acid, 4-thenoyl-2,3-dichlorophenoxyacetic acid, (1-oxo-2-methyl-2-phenyl-6,7-dichloro-5-indanyloxy)-acetic acid, 2-chloro-4-furfurylamino-5-carboxybenzenesulfonamide, 2-phenoxy-3-butylamino-5-carboxybenzenesulfonamide or 2-phenoxy-3-[3-(pyrrolyl)-propyl]-5-carboxybenzenesulfonamide.

5. A method of treating pathological conditions in a warm-blooded animal which are consequent on an impaired excretion of urine or urinary constituents, which consists in the administration of a therapeutically effective amounts of at least one 19-oxygenated steroid compound of the pregnane series of the formula

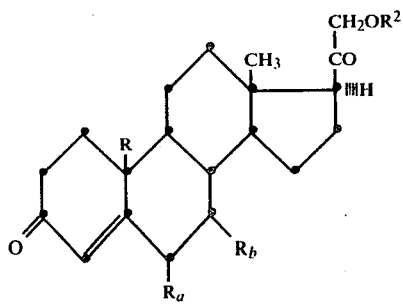

wherein
- $R_a$ represents a hydrogen atom, and
- $R_b$ represents an α-oriented lower alkanoylthio group, or
- $R_a$ and $R_b$ together represent a carbon-carbon bond or an α- or β-oriented methylene radical,
- R represents a free hydroxymethyl group or a hydroxymethyl group etherified by a lower alkyl or esterified by a lower alkanoyl; or represents a carboxyl group or a lower alkoxycarbonyl group, and
- $R^2$ represents a hydrogen atom or the acyl radical Ac of a carboxylic acid, or of a salt thereof, or of a 1,2-dihydro derivative thereof, as the aldosterone-antagonising component A on the one hand, and at least one diuretic component B which is unspecific in respect of electrolytes on the other hand, separately or in the form of a pharmaceutical composition as claimed in any one of claims 1 to 6.

6. A method according to claim 5, wherein the warm-blooded animal is man.

* * * * *

UNITED STATES PATENT AND TRADEMARK OFFICE
CERTIFICATE OF CORRECTION

PATENT NO. : 4,261,985
DATED : APRIL 14, 1981
INVENTOR(S) : MICHEL BIOLLAZ

It is certified that error appears in the above—identified patent and that said Letters Patent is hereby corrected as shown below:

CLAIM 5 SHOULD BE ENTIRELY CANCELLED.

CLAIM 5 should read:

"A method of treating pathological conditions in a warm-blooded animal which are consequent of an impaired excretion of urine or urinary constituents, which consists in the administration of a therapeutically effective amount of a composition according to Claim 1 to said animal in need thereof."

Signed and Sealed this

Ninth Day of February 1982

[SEAL]

Attest:

GERALD J. MOSSINGHOFF

Attesting Officer     Commissioner of Patents and Trademarks